United States Patent
Blümich et al.

(10) Patent No.: US 6,700,372 B2
(45) Date of Patent: Mar. 2, 2004

(54) METHOD FOR GENERATING MEASUREMENT SIGNALS IN MAGNETIC FIELDS

(76) Inventors: Bernhard Blümich, Bergstrasse 31, 52159 Roetgen (DE); Peter Blümler, Mainstrasse 6, 65474 Bischofsheim (DE)

( * ) Notice: Subject to any disclaimer, the term of this patent is extended or adjusted under 35 U.S.C. 154(b) by 0 days.

(21) Appl. No.: 10/079,687

(22) Filed: Feb. 19, 2002

(65) Prior Publication Data

US 2002/0079891 A1 Jun. 27, 2002

Related U.S. Application Data

(63) Continuation-in-part of application No. PCT/EP00/07948, filed on Aug. 16, 2000.

(30) Foreign Application Priority Data

Aug. 20, 1999 (DE) .......................... 199 39 626

(51) Int. Cl.⁷ ............................. G01N 3/00
(52) U.S. Cl. ........................................ 324/307
(58) Field of Search ................ 324/307, 309, 324/318, 322

(56) References Cited

U.S. PATENT DOCUMENTS

| | | | |
|---|---|---|---|
| 4,833,411 A | | 5/1989 | McDonald et al. |
| 5,304,930 A | | 4/1994 | Crowley et al. |
| 6,489,767 B1 | * | 12/2002 | Prado et al. ............... 324/318 |

OTHER PUBLICATIONS

G. Eidmann et al., The NMR Mouse, a Mobile Universal Surface Explorer; Journal of Magnetic Resonance; Series A 122, (1996) article #0185; 104–109.*

B. Blumich et al.; The NMR–Mouse: Costruction, Excitation, and Applications; Magnetic Resonance Imaging, vol. 16 (1998); 479–484.*

Markus Rokitta et al.; Portable Nuclear Magnetic Resonance Imaging System; Review of Scientific Instruments; vol. 71, No 11; 4257–4262.*

B. Blumich; The NMR–Mouse; Internet Publication 2000, 1–5.*

Bruker Optics Inc.; The minispec mouse; Brucker Optics Inc. Internet Publication; 1.*

B. Blumich et al.; Unilateral Nuclear Magnetic Resonance for Quality Control; Spectroscopy, 18(2) (2003); 18–34.*

B. Blumich; NMR Mouse; Institude of Technical Chemistry and Macromolecular Chemistry; Internet Publication (2003); 1–13.*

Blumich; Applications of the NMR–Mouse; AixNMR; Internet Publication (2003); 1–15.*

Zimmer, G, et al.: "Characterization of Cross–Link Density in Technical Elastomers by the NMR–Mouse", Solid State Nucl. Magn. Respectively., vol. 12, No. 2–3, 1998, pp. 183–190.

* cited by examiner

Primary Examiner—Edward Lefkowitz
Assistant Examiner—Dixomara Vargas
(74) Attorney, Agent, or Firm—Klaus J. Bach

(57) ABSTRACT

In a method for generating measurement signals in time constant inhomogeneous magnetic fields, which are produced by a NMR-MOUSE apparatus in the surrounding medium, a static magnetic polarization field $B_0$ and a pulsed magnetic polarization field $B_1$ are generated, whereby echo signals S are generated which are measured, and an additional pulsed or oscillating magnetic field $B_z$ is provided, which affects the echo signals S so as to generate contrasts for the measuring locations of the echo signals.

3 Claims, 3 Drawing Sheets

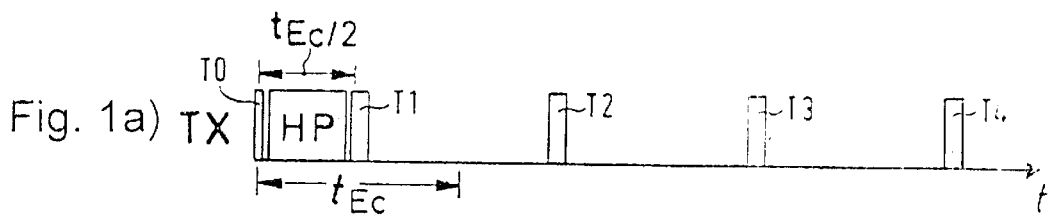
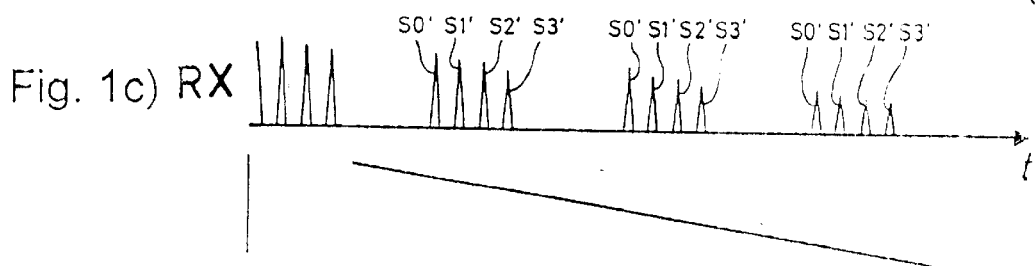
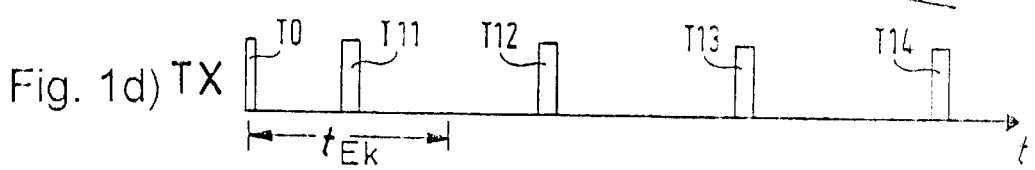
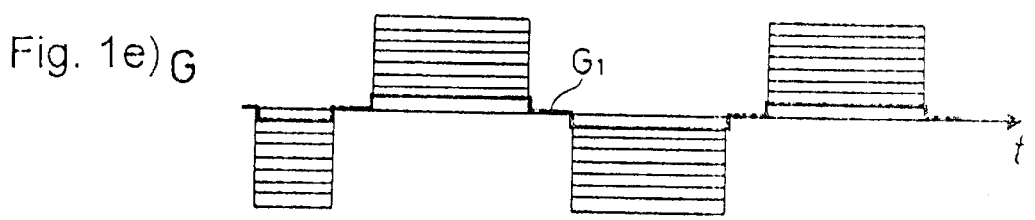
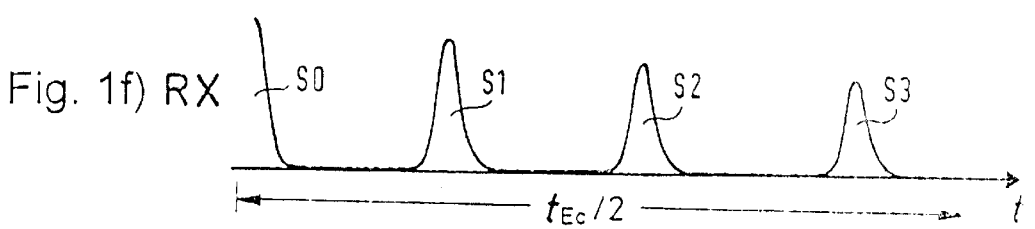

METHOD FOR GENERATING MEASUREMENT SIGNALS IN MAGNETIC FIELDS

This is a continuation-in-part application of pending international patent application PCT/EP00/07948 filed Aug. 16, 2000 and claiming the priority of German application 199 39 626.4 filed Aug. 20, 1999.

BACKGROUND OF THE INVENTION

The invention relates to a method for generating measurement signals in magnetic fields which are present in the area around an NMR-MOUSE apparatus and whose changes have to be measured. Herein, a time-constant magnetic polarization field $B_0$ is generated by magnets, for example electromagnets or permanent magnets, and a magnetic measurement field $B_1$ is generated by means of a high frequency oscillation circuit in a pulsed manner and the echo signals S generated in the surrounding medium are measured. The echo signals can be measured by the NMR-MOUSE apparatus in a time-dependent manner after a change of the magnetic field by one or several signal impulses generated by the NMR-MOUSE apparatus in each case after an echo time $t_E$. The measurement signal is generated in the magnetic field around the NMR-MOUSE apparatus where the components of the two magnetic field $B_0$ and $B_1$ extend normally to each other, that is, both fields have mutually perpendicular components.

The NMR-MOUSE apparatus (Nuclear Magnetic Resonance MObile Universal Surface Explorer) is a mobile measuring apparatus for nuclear magnetic resonance wherein the magnetic field generated and the measuring range provided by the measurement apparatus are disposed in the area around the apparatus. The NMR-MOUSE apparatus, which will simply be called "NMR-MOUSE", is therefore very suitable for determining data from the surrounding medium. It is used for the examination of spatial structures: It is possible to analyze therewith crystalline or glassy materials, as well as soft materials such as elastomers with regard to their molecular dynamics. Also, liquids as well as biological materials can be analyzed, see for example, G. Eidmann et al. "The NMR-MOUSE, a mobile universal surface explorer", Journal of Magnetic Resonance, 1996, pages 104/109, or A. Guthausen et al., "NMR-Bildgebung und Material Forschung" (NMR Imaging and material Research), Chemie in unserer Zeit, 1998, p.73/82. The time-constant static magnetic polarization field $B_0$ is usually generated with the NMR-MOUSE by one or several permanent magnets. The pulsed magnetic measuring field $B_1$, is the magnetic component of a high frequency field, which is formed by a coil as part of an electric oscillation circuit, wherein the coil usually serves also as the receiver coil for the echo signals to be measured. With the NMR-MOUSE, spatially homogenous magnetic fields are not necessary for the polarization of the nuclear magnetization in the permanent magnetic polarization field $B_0$ and for the generation and detection of the measuring signals.

NMR-MOUSE apparatus can therefore be small and relatively inexpensive in comparison with normal NMR apparatus. With the NMR-MOUSE, the form and size of the surrounding volume, which is nuclear magnetically implied in the surrounding field and which is to be detected by measuring the echo signals, on one hand, the orthogonal components of both magnetic fields $B_0$ and $B_1$ and, on the other hand, the specific bandwidth of the magnetic excitation of the material to be examined are defined. The pattern of the magnetic field lines can be changed by the dimensioning and the arrangement of the permanent magnets and of the coil of the electric high frequency oscillation circuit.

The spatial measuring range in the surrounding medium to be examined is variable three-dimensionally by displacement of the NMR-MOUSE, by deformation of the magnetic fields by additional windings and by changing the high frequency field. It is a disadvantage of the conventional apparatus of this type that the detection of the echo signals, which are generated in the surrounding medium by the transmitter signals, is very time consuming. There is an insufficient spatial resolution within the measuring range and the signals to be measured have too little contrast for distinguishing different material properties.

As it is known from DE 195 11 835 C2, the measuring time can be shortened by scanning the measuring range with frequency-selective high frequency pulses while utilizing the given constant magnetic field. In this way, a rapid measurement value yield is obtained, however the contrast achievable is insufficient for the representation of the medium to be examined, particularly for material examinations, where the requirements are very high.

It is the object of the present invention to generate, in time-constant inhomogeneous magnetic fields, measurement signals, which make it possible to detect in the measurement field several spatial points with a problem-specific contrast in a single measuring sweep.

SUMMARY OF THE INVENTION

In a method for generating measurement signals in time constant inhomogeneous magnetic fields, which are produced by a NMR-MOUSE apparatus in the surrounding medium, a static magnetic polarization field $B_0$ and a pulsed or oscillating magnetic polarization field $B_1$ are generated such that echo signals S occur which are measured, and an additional pulsed magnetic field $B_z$ is provided which affects the echo signals S so as to generate contrasts for the identification of the measuring locations where the echo signals originate.

With the additional magnetic fields, changes of the complete magnetic field in different spatial directions are obtained. If the high frequency impulses follow one another with a time spacing $t_{Ec}$, the additional magnetic fields are generated for the spatial coding only within the first half echo time $t_{Ec}/2$. The echo signals S formed thereby are subsequently called up several times with a time spacing $t_{Ec}$ to provide thereby for contrast. In this way several spatial points can be measured in a single measuring sweep for the detection of the surrounding volume, which is called a "multiplex advantage". Furthermore, the echo signals S are re-focussed several times with the impulses of the high-frequency oscillation circuit for generating contrasts. In addition to the multiplex advantage in the surrounding space, a multiplex advantage is also provided for the contrast measurements by weighting with typical NMR parameters (for example, by transverse relaxation time). For the examination of the surrounding field to be measured therefore not only a high number of measuring points can be scanned within a measuring time unit but the measuring points are determined at the same time with increased contrast so that, by generating the pulsed additional magnetic fields, a substantial qualitative improvement is achieved with respect to the analysis with the NMR-MOUSE as compared with conventional measuring methods.

Preferably, the pulsed additional magnetic fields are time-dependent in such a way that the polarity of the additional magnetic field reverses within the echo time $t_{Ec}$.

For generating the high frequency signals in the pulsed magnetic measuring field $B_1$, expediently the high frequency excitation according to the method of Carr, Purcell, Meiboon, and Gill, that is, the CPMG method, is used for the nuclear magnetization (see Guthausen et al. "Analysis of Materials by Surface NMR via MOUSE", J. Magn. Reson. 130, 1998 pages 1/7). Also, other known NMR-echo procedures for contrast variation may be utilized and may be appropriate, whereby echo signals can be generated whose amplitudes are, to a large extent, independent of the inhomogeneity of an existing permanent magnetic field. The influence on the measuring signal resulting from the inhomogeneous static magnetic field as it is present in the polarization field $B_0$ of the NMR-MOUSE is eliminated in this way. The effect of the additional magnetic field $B_2$ on the echo signal S can therefore be determined with little interference.

A variation in the solution of the object stated above based on the method described resides in the generation of oscillation-modulated additional magnetic fields $B_z(+)$ (for example, oscillation modulated gradient fields) and the timing $t_E$ of the high frequency impulses, and the modulation of the oscillating additional magnetic field are timed relative to each other in such a way that the time interval $t_E/2$ between two successive high frequency impulses with rotational angles α and subsequent β (for example β=2α) corresponds to half the oscillation time of the modulation function of the oscillating additional magnetic field.

In this case, the two high frequency impulses are emitted as transmitter signals at the zero passage of the modulation function. During the next following zero passage of the modulation function, the high frequency impulse is omitted and, instead, the echo signal acq provided at this point in time (acq=acquisition) is detected. The high frequency impulse detection sequence α-$t_E$/2-β-$t_E$/2-acq is repeated several times wherein the additional magnetic field is amplitude-modulated after completion of each sequence. The measuring field is scanned in this way spatial point by spatial point, wherein, if necessary, missing spatial points are iteratively added for the completion of the analysis of the surrounding medium.

In order to be able to start after each sequence again at the starting point, in a refinement of the invention, the modulation function for the additional magnetic field is refocused after each detection and passage of a sequence through a half wave with an opposite, and twice the, amplitude. The k-space, or respectively, the measuring field, is interrogated in this way in a non-sequential manner for Cartesian space coordinates; from –$k_1$ a jump occurs to +2 $k_1$ and then to –3 $k_1$ and to 4 $k_1$, etc. For the $k_1$ value, the time integral of the gradient modulation function in the first time interval $t_E$ is the determinative factor. If then an iterative completion of open k-points in the measuring field is insufficient for the examination of given structure of the material, the measurement can be repeated with a sequence having a reversed sign, whereby then the space points $k_1$, –2 $k_1$, +3 $k_1$, –4 $k_1$, etc . . . are scanned. If the gradient modulation of the additional magnetic field occurs at constant frequency, the amplitude modulation is easily realized by a resonant control of the oscillation circuit.

Below, the invention will be described in greater detail on the basis of examples in connection with the schematic drawings.

BRIEF DESCRIPTION OF THE DRAWINGS

FIGS. 1a–f show a multiplexing procedure,

FIG. 3b is a cross-sectional view of the NMR-MOUSE taken along line b—b of FIG. 3a.

DESCRIPTION OF A PARTICULAR EMBODIMENT

Figure 2:
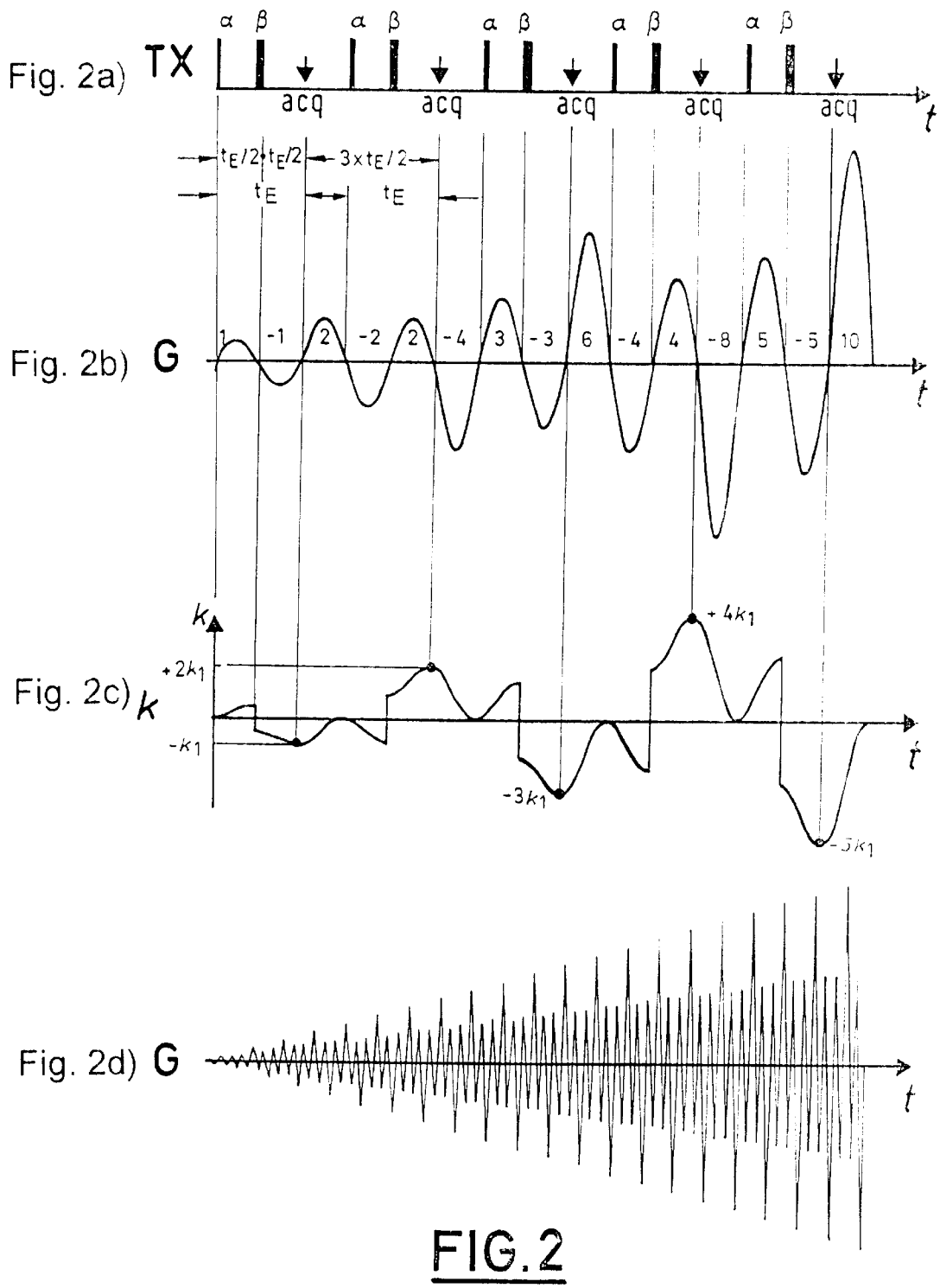
FIGS. 2a–c show an oscillating gradient field.

FIGS. 1a to 1f show schematically the multiplexing procedure. They indicate the timed occurrence of subsequent signal pulses. In FIG. 1a, the pulsed transmitter signals TX of the high frequency oscillating circuit for generating the magnetic measuring field $B_1$ are schematically shown.

"Pulsing" of the transmitter signals or "pulsing" of the high frequency magnetic field means that the measuring field $B_1$ is generated in a predetermined timed manner, in the example with a timed spacing of $t_{Ec}$, by excitation of the radio frequency coil for a short period in a pulsed manner. At first pulsing of the radio frequency oscillating circuit with transmitter signals T0, T1 in the first interval $t_{Ec}/2$ which will be designated below as preparation period is followed subsequently by transmitter signals T2 to TN of the high frequency oscillation circuit each with a time interval $t_{Ec}$. In FIG. 1b, the gradient signal G for generating the additional magnetic field $B_z$ is shown and in FIG. 1c the receiver signal RX is indicated, which can be measured on the basis of the echo signals S which are formed in the whole magnetic field by super position of the constant magnetic, in the given example permanent magnetic, polarization field $B_0$, the pulsed magnetic field $B_1$ and the also pulsed additional magnetic field $B_z$ ($B_z$=Gr, wherein G=d$B_z$/dx=constant, and r=position vector).

FIGS. 1d, 1e and 1f show transmitter-, gradient-, and receiver signals during the preparation period, which are spaced timely differently from the FIGS. 1a, 1b, and 1c. Indicated are those signals which are sent and received within the first time interval $t_{Ec}/2$. In FIGS. 1a, 1b and 1c, those signals are indicated in the preparation period schematically as blocks; FIG. 1a shows the transmitter signals TX of the high frequency oscillation circuit as block HP (see time-spaced in FIG. 1d with T11, T12, T13, T14); FIG. 1b shows the gradient field G of the additional magnetic field $B_z$ with reversed sign of the gradient as block GP (see time spread in FIG. 1e). The transmitter signals TX of the high frequency oscillation circuit are generated in the preparation period in a clocked manner with a timing $t_{Ek}$. The receiver signal RX, which occurs with the superposition of the magnetic fields $B_0$, $B_1$ and $B_z$ within the preparation period $t_{Ec}/2$ is shown in FIG. 1f in an expanded manner, wherein as the first signal S0, the FID (Free Induction Decay) signal is given, which is generated by the first transmitter signal T0 of the high frequency oscillation circuit. The FID signal is then followed by the echo signals S that is S1 to S3.

As apparent from FIGS. 1a to 1f, the additional magnetic field $B_z$, which is formed in the example by reversal of the sign of the gradient field, is generated only in the first time interval $t_{Ec}/2$, that is, during the preparation period. In the subsequent time intervals, the additional echo signals S0' to S3' are measured on the basis of the high frequency excitations T1, T2, T3, without the additional magnetic field being again switched on, with amplitude values which become weaker in accordance with the relaxation time, see FIG. 1c. The echo signals S' can be utilized during the image generation for providing contrasts.

In the example, the CPMG method is used for the high frequency excitation of the nuclear magnetization in the measuring field $B_1$. The influence of the time-constant inhomogeneities of the polarization field $B_0$ generated by the permanent magnet fields of the NMR-MOUSE on the echo signals S to be received is eliminated as a result. The additional magnetic field $B_z$ is timely so switched that its effect on the echo signal remains. In the most simple case, a sign reversal is provided to this end for the additional magnetic field within the time interval $t_{Ec}/2$ as it is shown in FIG. 1e. Consequently, with each echo in the CPMG-sequence, further spatial information is obtained in the wave vector space or k space, which is Fourier-conjugated to real space with a simple gradient field. If, as in the exemplary embodiment, additional gradients G are introduced and, in addition to the FID signal S0, three CPMG echos S1 to S3 are generated in the presence of high frequency transmitter impulses TX within the preparation period, in the second and all further time intervals $t_{Ec}$ with the echoes S0' to S3' as they are schematically shown in FIG. 1c, each time four space points are sampled in the k space. The four CPMG echoes generated within the echo time $t_{Ec}$ are repeatedly recalled with the gradient field switched-off as indicated earlier. Their space encoding via the k space is utilized for the definition of the contrast. How many subsequent time intervals can be utilized for the determination of space points depends on the veiling of the echo signals by instrument noise.

In the example according to FIGS. 1a–f, four values of the k space with constant amplitude value for the gradient pulses G (see FIG. 1e, gradient value $G_1$ indicated by heavy line), are called up, that is, k=0, $k_1$, 2 $k_1$, 3 $k_1$. Further values of the k space are obtained by repetition of this measurement procedure with other values of the gradient pulse G, which are determined for example in accordance with the arrow direction as indicated in FIG. 1e for increasing gradient values G.

For generating the echo sequences, different methods may be employed such as 180° impulses according to Hahn as they are used in the CPMG sequence. But also, impulses for dipolar echoes may be utilized, see in this regard Guthausen et al. as cited earlier. Depending on how the signal is provided, different signal weighting and, as a result, different contrasts are obtained.

By generating multiple echoes, which, in proportion, have the character of Hahn echoes, the measurement becomes independent of the time-constant inhomogeneities of the permanent magnetic fields. Expensive magnets for generating homogeneous magnetic fields are therefore not needed. In one measuring sweep, several spatial points in the k space are sampled. In this respect, the method is similar to the SPARE method (Single Point imAging with Relaxation Enhancement, see D. J. O. McIntyre et al. "A Robust Method for Magnetic Resonance Imaging in Inhomogeneous Fields". J. Magn. Reson. 130, 1998, pages 58/62).

FIGS. 2a to 2d show the high frequency impulses TX, which follow one another with a selected echo time $t_E$ in an impulse sequence $\alpha$–$t_E/2$–$\beta$–$t_E/2$–acq, wherein a respective detection acq of the echo value occurs following excitation pulses generated subsequently with a time spacing of $t_{E/2}$ and with a rotational angle $\alpha$ and a refocusing angle $\beta$. The data acquisition time acq is indicated in FIG. 2a by an arrow. For Hahn echoes, the refocusing angle $\beta=2\alpha$, wherein $\alpha=90°$, that is, $\beta=180°$.

FIG. 2b shows the oscillation of the gradient G(t) of the additional magnetic field $B_z(t)$, which, in the example, is superposed for the spatial resolution and which oscillates with constant frequency and is modulated by changing the amplitude. The frequency of the gradient function, or, respectively, the oscillating additional magnetic field $B_z(t)$ and the time spacing $t_E$ of the impulse sequence between the first excitation pulse $\alpha$ and the detection acq are so adjusted to each other that the excitation pulses $\alpha$, $\beta$ and the detection acq are always centered on a zero passage of a half wave of the oscillating additional magnetic field. The time distance $t_E$ of the impulse and the detection is therefore $t_E=1/\nu$, wherein $\nu=$the frequency of the oscillating additional gradient field $G_{(t)}$. The oscillating additional gradient field is time-modified in its amplitude in such a way that, with subsequent echoes, different spatial points in the k space are sampled. In the example, the amplitude of the additional magnetic field is so modified that, after a particular sequence, the gradient integral becomes zero after a time $3 \times t_E/2$ and the starting point of the k space to be measured is again reached at k=0. To this end, after each detection, the amplitude is doubled with a reversed value (see FIG. 2b, the value sequence +1, −1, +2, −2, +2, −4, +3, −3, +6 etc). The curve of the gradient function modified in this way over an extended period is represented in FIG. 2d. It shows—time compressed with respect to the values of FIGS. 2a to 2c—a gradient modulation over more than 40 impulse sequences.

After excitation by the first high frequency impulse $\alpha$ and refocusing by the second high frequency impulse $\beta$, the amplitude of the echo is measured in each sequence at the point in time $t_E$ at the zero passage of the oscillating additional magnetic field. With the values detected in this process, the k space is scanned. The subsequent measuring points of the k space are marked in FIG. 2c for each detection point acq. As a result of the described gradient modulation at the completion of each time period $3t_E/2$, each measuring cycle starts in the example after each pulse sequence in the k space again at the starting point of the measurement (see FIG. 2c, k=0 at the beginning of each impulse sequence). In this way, the k space is interrogated in a non-sequential manner for Cartesian coordinates. In the example in FIG. 2c for the value $k=k_1$, the values $-k_1$, $+2k_1$, $-3k_1$, $+4k_1$, etc., are determined one after the other. The values of the k space which were not determined in the process can be determined iteratively or, for a complete sampling of the k space, by a repetition of the measuring procedure for example with pulse sequences of a reversed sign wherein then the values $+k_1$, $-2k_1$, $+3k_1$, $-4k_1$ etc. are determined in the k space. The gradient modulation occurs in the example at constant frequency so that a resonant control is sufficient.

This procedure is in its concept basically similar to the procedure employed in the imaging process according to the FAST procedure (See M. Glyngell, J. Magn. Reson. Imag. 6, 1988, page 415) it operates however with a continuously oscillating gradient of a basic frequency.

Figure 3A:
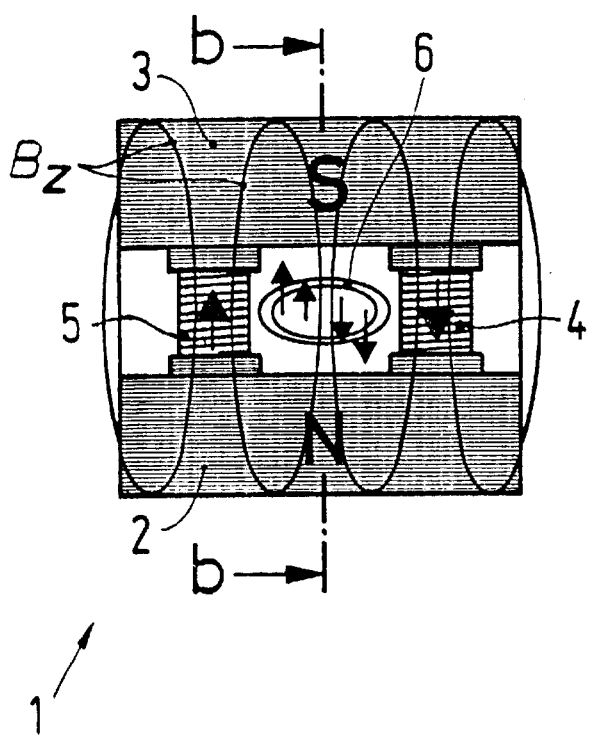
FIG. 3a is a top view of an arrangement of a NMR-MOUSE for performing the method according to the invention.
Figure 3B:
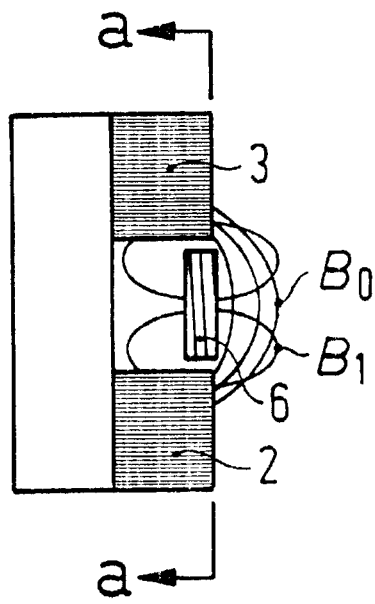

FIGS. 3a and 3b show schematically a NMR-MOUSE, which is suitable for performing the method according to the invention.

For a polarization of the nuclear magnetic moments in the material to be examined and for the generation of measuring signals, the NMR-MOUSE includes spatially inhomogeneous magnetic fields. As apparent from FIGS. 3a and b, in an NMR-MOUSE two gradient coils 4 and 5 are placed between oppositely magnetized permanent magnets 2, 3 with permanent magnetic poles N and S, and a high frequency coil 6 is placed between the gradient coils 4 and 5. By means of the high frequency coil 6, a magnetic measuring field $B_1$ can be superimposed at given time intervals in a pulsed manner, on the polarization field $B_0$. The static polarization field $B_0$ generated between the permanent magnet poles can be superimposed, by means of a radio frequency coil, on a magnetic measuring field $B_1$, which is pulsed in time and constitutes the magnetic part of a radio frequency field, that is generated and received by a radio frequency coil as part of an electrically oscillating circuit. For the pulsing of the magnetic measuring field $B_1$, the magnetic field is generated with a predetermined clock timing by excitation of the high frequency coil over a short period in a pulsed manner. With the gradient coils 4, 5,—also pulsed—a magnetic gradient field is superimposed on the magnetic field as additional magnetic field $B_z$. FIG. 3a shows schematically the field lines of the additional magnetic field $B_z$ generated by the gradients. Form and size of the surrounding volume, which is implicated around the NMR-MOUSE in a nuclear magnetic manner and is to be detected by measuring the echo signals and which, in this way, represents the measuring sensitive volume area, is defined for each apparatus on one hand by the specific bandwidth of the magnetic high frequency excitation and, on the other hand, by the orthogonal components of the two magnetic fields $B_0$ and $B_1$. The shape of the magnetic field lines and consequently, the size of the signal-providing volume range can be varied by appropriate dimensioning and arranging of the permanent magnets and the coil of the electric high frequency oscillation circuit as well as the utilization of additional coils.

By means of the gradient coils 4, 5, an additional magnetic field $B_z$ with a field gradient which is tangential to the outer surface of the NMR-MOUSE 1 and normal to the polarization field $B_0$ is generated in addition to the permanent magnetic polarization field $B_0$. This additional magnetic field is pulsed in a clocked manner to provide the spatial resolution (phase coding of the space location information). The high frequency coil 6 is so arranged that the field lines of the polarization field $B_0$ and the field lines of the magnetic measuring field $B_1$ generated by the high frequency coil extend in the measuring sensitive volume area normal to each other. The orthogonal components of the two magnetic fields $B_0$ and $B_1$ provide for the measuring signal. For an excitation and the detection of the measuring signal, the same high frequency coil is used.

In FIGS. 3a and 3b, the magnetic fields and the signal impulses generated are represented only in a one-dimensional manner in one of the spatial directions. Of course, the magnetic fields are superimposed in all three spatial directions. With additional magnetic coils additional magnetic fields with gradients in the other spatial directions can be generated for two-dimensional and three-dimensional spatial resolution. The echo signals can be retrieved accordingly in a three-dimensional way and the measuring methods described can be expanded to 2 and 3 space coordinates.

What is claimed is:

1. A method for generating measurement signals in magnetic fields which are generated by an NMR MOUSE apparatus in a surrounding medium and whose changes are measured, said method comprising the steps of: generating a static magnetic polarization field $B_0$, and, by means of a high frequency oscillation circuit, a pulsed magnetic measuring field $B_1$ including high frequency impulses (T0, T1, T2 to Tn) occuring with a time spacing $t_{Ec}$, generating within a preparation period $t_{Ec}/2$ an additional pulsed magnetic field $B_z$ whose polarity is changed within the preparation period after each high frequency pulse (T11, T12, T13, T14) and which is superimposed on said static magnetic measuring field thereby causing in the surrounding medium echo signals (S), measuring the echo signals (S) after an echo time $t_E$, determining the orthogonal components of the echo signals magnetic polarization field $B_0$ and of the pulsed magnetic measuring field $B_1$ for determining the measurement signals, and repeatedly refocusing the echo signals S generated within the preparation period $t_{Ec}/2$ without pulsed additional magnetic fields by a gradient having twice the value and the opposite direction of the previous half wave gradient for providing contrast.

2. A method according to claim 1, wherein CPMG echoes are generated as echo signals S.

3. A method for generating measurement signals in magnetic fields which are generated by an NMR-MOUSE apparatus in the surrounding medium and whose changes are measured, said method comprising the steps of generating a static magnetic polarization field $B_0$ and, by means of a high frequency oscillation circuit, a pulsed magnetic field $B_1$, which is superimposed on said stationary magnetic polarization field $B_0$, determining the echo signals S generated thereby in the surrounding medium, which can be measured after an echo time $t_E$, wherein the orthogonal components of the two magnetic fields $B_0$ and $B_1$ provide for the measuring signals, generating oscillation modulated additional magnetic fields $B_Z(t)$, adjusting high frequency impulse and modulation of the additional magnetic field with respect to each other in such a way that the time distance $t_E/2$ between two subsequent high frequency impulses with rotational angles $\alpha$ and $\beta$ corresponds to half the oscillation time of a modulation function of the additional magnetic field and that the high frequency impulses form transmission signals which are always provided during zero passage of the modulation function, detecting the echo signal (S) generated in the surrounding medium during the subsequent zero passage of the modulation function after issuance of the two high frequency transmission signals, repeating subsequently the high frequency impulse detection sequence $\alpha - t_E/2 - \beta - t_E/2 - acq$ provided thereby, and re-focussing the additional magnetic field by amplitude-modulating a gradient with an amplitude which has twice the value and the opposite direction of the previous gradient half wave.

* * * * *